United States Patent [19]

Oberhardt et al.

[11] 4,280,815
[45] Jul. 28, 1981

[54] ELECTROCHEMILUMINESCENT IMMUNOASSAY AND APPARATUS THEREFOR

[75] Inventors: Bruce J. Oberhardt, Mishawaka, Ind.; Neil Wotherspoon, New York, N.Y.

[73] Assignee: Technicon Instruments Corporation, Tarrytown, N.Y.

[21] Appl. No.: 49,818

[22] Filed: Jun. 18, 1979

[51] Int. Cl.³ .................... G01N 21/62; G01N 33/54
[52] U.S. Cl. .................... 23/230 B; 23/915; 23/927; 422/55; 422/68
[58] Field of Search .................... 23/230 B, 915, 927; 424/12; 422/50, 55, 57, 61, 68; 204/1 T, 1 Y, 149

[56] References Cited

U.S. PATENT DOCUMENTS

| | | | |
|---|---|---|---|
| 2,805,191 | 9/1957 | Hersch | 204/1 Y |
| 3,853,467 | 12/1974 | Giaever | 424/12 X |
| 4,013,527 | 3/1977 | Idota et al. | 204/149 X |
| 4,041,146 | 8/1977 | Giaever | 424/12 X |
| 4,089,761 | 5/1978 | Ramer | 204/149 |
| 4,104,029 | 8/1978 | Maier, Jr. | 424/12 X |
| 4,118,307 | 10/1978 | LaBarre | 204/149 X |
| 4,172,827 | 10/1979 | Giaever | 23/230 B |

*Primary Examiner*—Arnold Turk
*Attorney, Agent, or Firm*—S. P. Tedesco

[57] ABSTRACT

A method and apparatus for performing a chemiluminescent immunoassay featuring electrochemical techniques to generate an oxidant used to trigger the chemiluminescence of the labelled immunoreactant. The generation of the oxidant is precisely controlled and the oxidant precisely and uniformly delivered to provide a more accurate, precise and sensitive assay.

21 Claims, 22 Drawing Figures

FIG. 3a
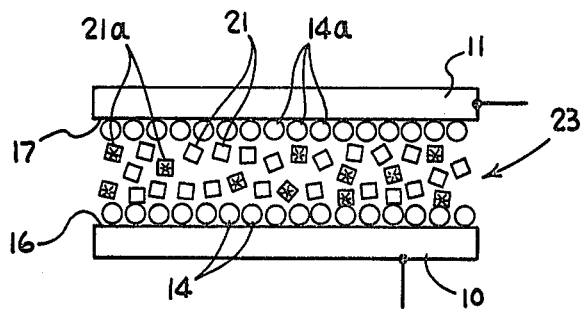
FIG. 3b
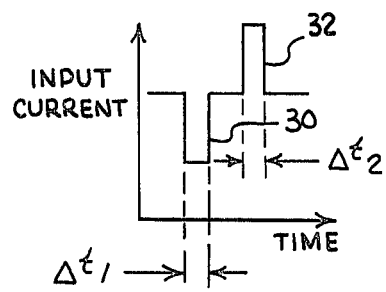
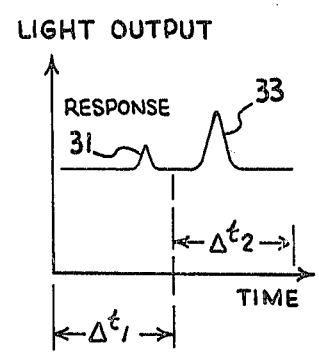
FIG. 3c
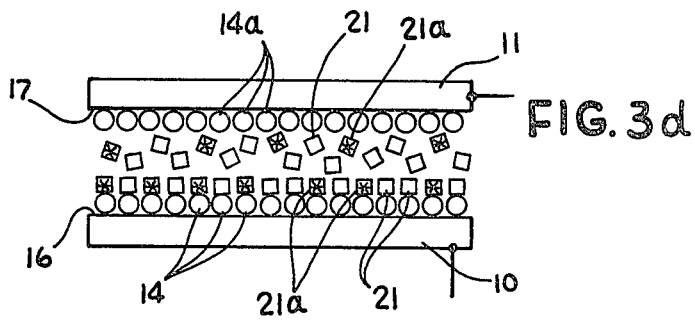
FIG. 3d
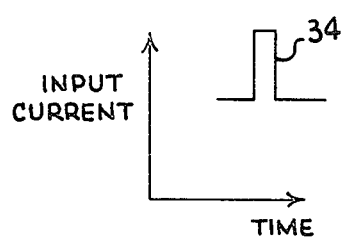
FIG. 3e
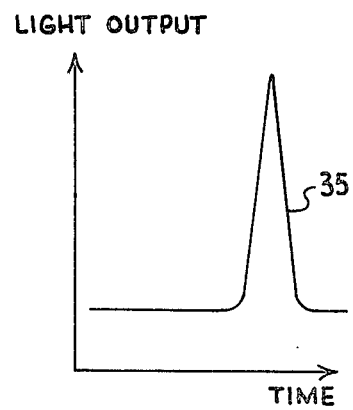
FIG. 3f

ELECTROCHEMILUMINESCENT IMMUNOASSAY AND APPARATUS THEREFOR

FIELD OF THE INVENTION

The invention relates to chemiluminescent immunoassays and, more particularly, to using solid phase techniques for improving the sensitivity, accuracy and precision of these assays.

BACKGROUND OF THE INVENTION

Chemiluminescent immunoassay techniques generally comprise forming a reactive mixture of a known amount of antibody with a biological sample containing an unknown amount of antigen to be determined, or vice versa. A known amount of a competing immunoreactant, which is labelled with a chemiluminescent label, is added to the reactive mixture. The reactive mixture is incubated, the labelled immunoreactant competing with the sample immunoreactant for the known amount of the complementary reactant, as well known in the art.

After incubation, the excess unbound labelled immunoreactant is usually separated from the reactive mixture, and an oxidant is added to trigger the chemiluminescence of the bound labelled immunoreactant. The measured level of chemiluminescence is indicative of the amount of the antigen in the biological sample.

Chemiluminescent immunoassays require that very precise amounts of the various reagents and/or reactants be used, because of the usually low concentrations of the sample immunoreactant.

The invention has as one of its purposes to precisely control the amount of oxidant used to trigger the chemiluminescence, and to precisely and uniformly deliver the oxidant to the bound chemiluminescent immunoreactants to provide a more sensitive, accurate and precise immunoassay procedure.

Additionally, the invention teaches a method of performing chemiluminescent immunoassays in avoidance of the separation step, a usually inconvenient and time-consuming exercise.

The invention further seeks to teach conservation or reuse of some of the reagents or reactants for subsequent immunoassy tests, since many of the reagents employed are expensive.

SUMMARY OF THE INVENTION

The invention relates to the use of solid phase techniques for performing chemiluminescent immunoassays. As a first step in the inventive procedure, a biological sample containing the immunoreactant to be determined is mixed with a competing immunoreactant which carries a chemiluminescent label. This mixture is introduced between two electrodes, whose surfaces are in close proximity. At or near one of the electrode surfaces, generally the anode, a complementary immunoreactant to the solution immunoreactants is immobilized. The complementary immunoreactant may be in a dehydrated form, so as to provide a long shelf life for the reagent prior to use, and rehydrated by the immunoreactant solution.

The mixture of competing immunoreactants is then incubated to cause a competitive binding to occur. After a suitable incubation period, the excess or unbound immunoreactants can be separated leaving the remaining reacted immunoreactants bound to the electrode.

The oxidant needed to trigger the chemiluminescence, usually peroxide or monatomic oxygen, is then generated at one of the electrode surfaces by applying a controlled voltage across the electrodes. The chemiluminescence which results from the oxidation of the chemiluminescent label is measured to determine the amount of immunoreactant being measured in the sample.

The above method improves the sensitivity, accuracy and precision of the chemiluminescent immunoassay procedure, by generating and delivering a precise amount of oxidant to the bound immunoreactants by control of the voltage applied across the electrodes.

The immunoreactants bound to the oxidant generating electrode (anode) are directly in contact with the oxidant as it is being generated at the electrode surface. The chemiluminescence which is generated is confined to a very localized area between the two adjacent electrode surfaces, which reduces the geometric loss of light signal and improves the accuracy and reliability of the measurement.

One or both of the electrodes may be transparent, so that the chemiluminescent light emission may be measureable directly at the reaction site. Also, one of the electrodes may be made an integral part of an optical detector to minimize loss of light.

The separation step of the prior art procedures may be eliminated by generating a small amount of oxidant at the beginning of the incubation cycle. This is done to determine the background level of any unbound labelled immunoreactant which is close enough to the generating electrode to chemiluminescence. By subtracting any signal produced by any unbound components from the total reaction signal, the need to perform a separation or washing step is eliminated. Another technique for eliminating the separation step may be achievable by time analysis of the signal produced in response to electrical triggering. Chemiluminescently labelled species bound to complementary immunoreacting species would be closer in proximity to the site of generation of oxidizing species and, therefore, produce a detectable signal earlier in time than the signal produced by the unbound chemiluminescent species situated further from the anode, which signals can be discriminated on a time basis.

The immunoreactive reagents are expensive, and it would be desirable, therefore, to reuse them. The invention can reuse the immobilized electrode-supported immunoreactant, by removing any bound immunoreactants after each assay, leaving the electrode supported immunoreactant available for reuse. This may be accomplished by dissociating the reacted antigens, for example, from the antibody bound to the electrode.

It is an object of this invention to provide an improved chemiluminescent immunoassay;

It is another object of the invention to provide a method and apparatus for performing a solid phase chemiluminescent immunoassay;

It is another object of the invention to provide a method and apparatus for performing a solid phase chemiluminescent immunoassay;

It is still another object of this invention to perform a more sensitive, accurate and precise chemiluminescent immunoassay by carefully controlling the amount, uniformity and timing of delivery of the oxidant required to trigger the chemiluminescence;

It is a further object of the invention to provide a method and apparatus for conducting a convenient, low-cost chemiluminescent immunoassay.

These and other objects of this invention will be better understood and will become more apparent with reference to the following detailed description taken in conjunction with the accompanying drawings.

BRIEF DESCRIPTION OF THE DRAWINGS

FIG. 2a shows a reaction mixture being formed between the electrodes;

FIG. 2b shows an electrical pulse which is applied to the anode of FIG. 2a;

FIG. 2c is a graphical representation of the light output produced by the pulse of FIG. 2b;

FIG. 2d illustrates the mixture of FIG. 2a after incubation;

FIG. 2e depicts an electrical pulse which is applied to the anode of FIG. 2d;

FIG. 2f is a graphical representation of the light output produced by the pulse of FIG. 2e;

FIG. 2g is a graphical representation of the net light output;

FIGS. 3a through 3f depict an alternate schematic embodiment to the method illustrated in FIGS. 2a through 2g;

FIG. 3a shows a reactive mixture being introduced between a pair of modified electrodes similar to those shown in FIGS. 1 and 2a;

FIG. 3b shows an electrical pulse which is applied to the electrodes of FIG. 3a;

FIG. 3c is a graphical representation of the light output produced by the pulse of FIG. 3b;

FIG. 3d illustrates the reactive mixture of FIG. 3a after incubation has occurred;

FIG. 3e shows an electrical pulse which is applied to the anode of FIG. 3d;

FIG. 3f shows a graphical representation of the light output produced by the pulse of FIG. 3e;

DETAILED DESCRIPTION OF THE INVENTION

Generally speaking, the invention contemplates using solid phase techniques to perform a chemiluminescent immunoassay. For the sake of brevity, the discussion will be directed to a reaction involving labelled antigens competing with sample antigens for complementary antibodies. However, it should be realized that the invention can easily apply to a test for sample antibodies competing with labelled antibodies for complementary antigens.

Figure 1:
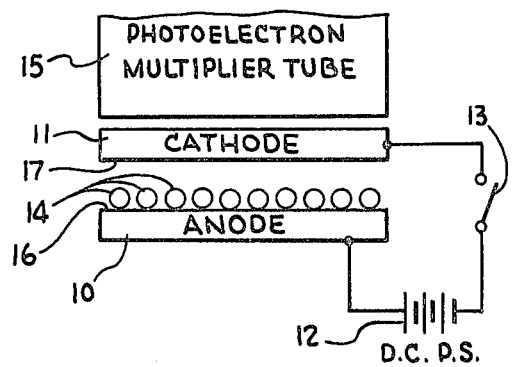
FIG. 1 is a schematic view of the apparatus used in the solid state chemiluminescent immunoassay of this invention.
Figure 1B:
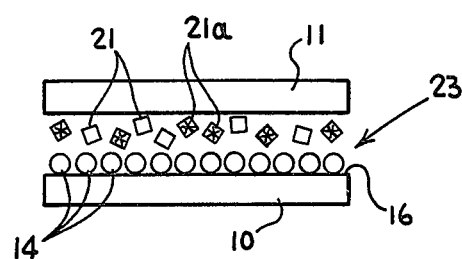
FIG. 1b is a schematic view of the reactive mixture formed between the electrodes of the apparatus depicted in FIG. 1.

Now referring to FIG. 1, a schematic view is shown of the solid state apparatus of this invention. The solid state apparatus generally comprises two adjacent electrodes 10 and 11. The electrode 10 being an anode and the electrode 11 being a cathode by virtue of the polarity of the direct current voltage source 12 to which they can be coupled via switch 13.

Antibodies 14 are supported or immobilized upon the anode 10. The antibodies may be attached or bound to the anode 10 by techniques known in the art, for example:

(1) Antibodies can be covalently bound to a metal or metal oxide surface forming part of the surface of the anode 10. Techniques for accomplishing this have been developed by General Electric Company, as described in the articles: I. Giaever, *Visual Detection of Carcinomebryonic Antigen on Surfaces*, Reprint No. 7891 and J. I. Treu, *Mie Scattering, Maxwell Garnett Theory, and the Giaever Immunology Slide*, Reprint No. 8018, General Electric Company, Corporate Research and Development, P. O. Box 43, Schenectady, N.Y. 12301 U.S.A.

(2) Antibodies 14 may be impregnated in a thin gel material such as agarose (not shown) which can be layered upon the surface of anode 10. Methods for coupling to gels may be found in the affinity chromatography literature, for example: Cuatrecasas, P., *J. Biol. Chem.* 245, 574 (1970); Cuatrecasas, P., Anfinsen, C. B., *Methods Enzymol.*, 22, 345 (1971); Cuatrecasas, P., *J. Biol. Chem.*, 245,3059 (1970); Cuatrecasas, P., Wilchek, M., Anfinsen, C. B., *Proc. Nat. Acad. Sciences USA*, 61, 636 (1968); Lang, T., Suckling, C. J., Wood H.C.S., *J. Chem. Soc.*, 19, 2189 (1977).

(3) Antibodies 14 can be impregnated or attached to a thin membrane (not shown) which can be layered over the surface 16 of anode 10, etc.: Axon, R., Porath, J., Ernback, S., *Nature*, 214, 1302 (1967); Hirata, A. A. and Brandrics, M. W., *J. of Immunology*, 100, 641 (1968).

Cathode 11 is preferably made transparent, so as to pass light due to the chemiluminescence of the assay to a photoelectron muliplier tube 15. For example, cathode 11 may be made of glass which is coated with a thin transparent layer of electrically conductive material such as gold or tin oxide, which is deposited on the glass surface of cathode 11.

Figure 5:
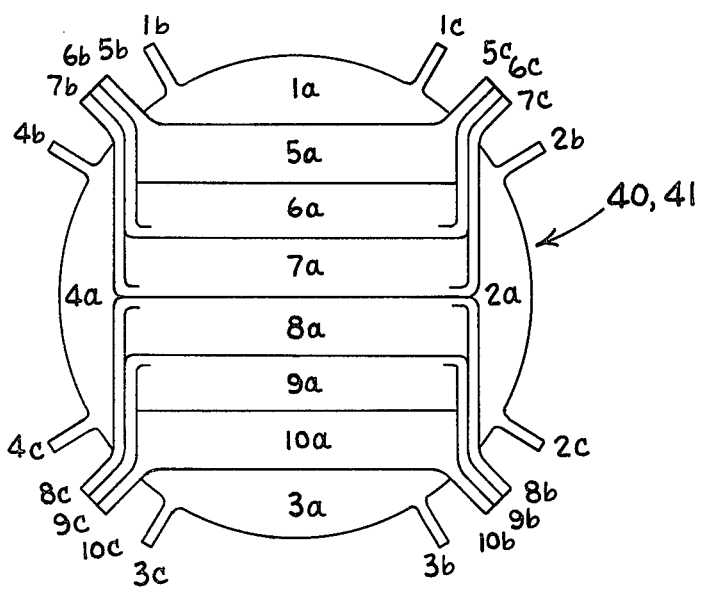
FIG. 5 is a plan view of another embodiment of the apparatus of FIG. 1, wherein a multiplicity of reactions can be simultaneously performed.

In another embodiment, the cathode 11 may be made integral with the photoelectron multiplier tube 15, by coating the glass surface of tube 15 with the conductive material (see FIG. 5).

In still another embodiment, the cathode may be made in the form of a wire mesh or screen (not shown).

Figure 1C:
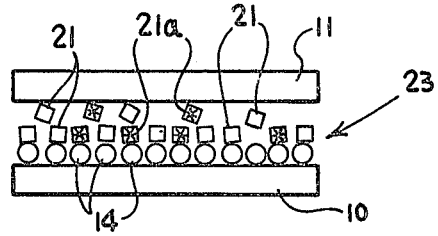
FIG. 1c shows a schematic view of the reactive mixture of FIG. 1b, after incubation has occurred.
Figure 1D:
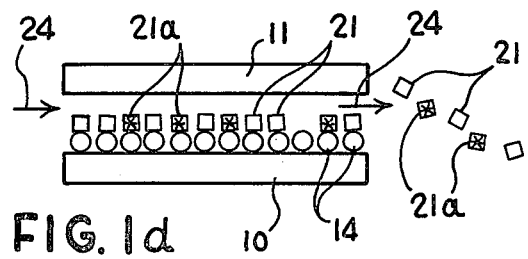
FIG. 1d illustrates a schematic view of the incubated mixture of FIG. 1c, with the unreacted or unbound immunoreactants being washed from between the electrodes.
Figure 1E:
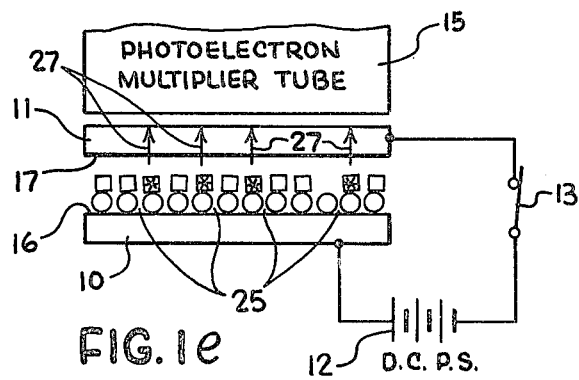
FIG. 1e depicts a schematic view of the incubated and washed immunoreactants of FIG. 1d, the subsequent generation of oxidant for chemiluminescing the reactive products, and the measurement of the chemiluminescent light level.
Figure 1A:
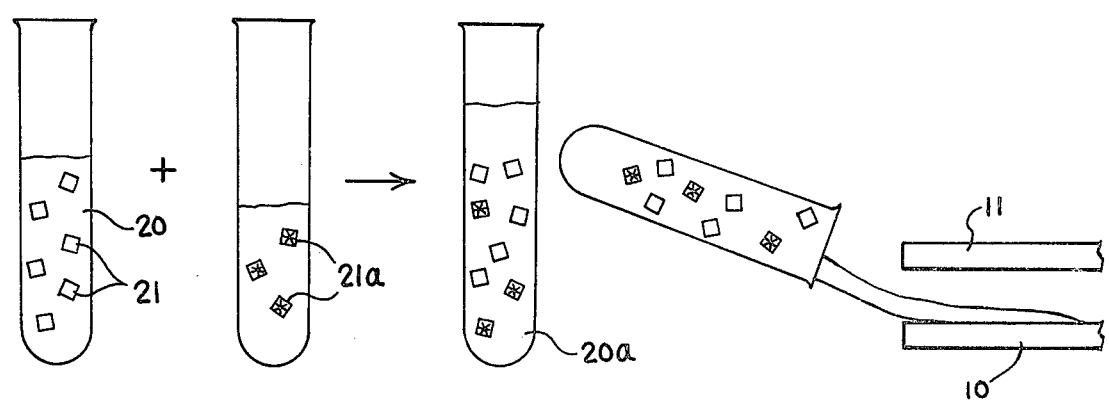
FIG. 1a is a schematic view of the mixing of the sample solution with the labelled immunoreactant solution, and the subsequent introduction of the mixed solutions between the electrodes of the apparatus shown in FIG. 1 to form a reactive mixture.

Referring to FIGS. 1a through 1e, the method of this invention is sequentially shown. FIG. 1a shows a biological sample 20 containing an unknown amount of antigens 21, which is to be determined. To the sample solution 20 is added a known amount of chemiluminescently labelled antigen 21a of the same type of antigen as those of solution 20 yielding solution 20a. The labelling of immunoreactants with chemiluminescent substances is taught by the following article: Schroeder, H. R. and Yeager, F. M., *Analytical Chemistry*, 50, 1114 (1978). Solution 20a is introduced between the electrodes 10 and 11 of the apparatus of FIG. 1 as shown to form the reactive mixture 23 illustrated in FIG. 1b. The reactive mixture 23 comprises (in summary) an unknown amount of sample antigen 21 to be determined, a known amount of competing chemiluminescently labelled antigen 21a, and a known amount of complementary antibodies 14 immobilized upon the surface 16 of anode 10.

FIG. 1c shows the reaction mixture 23 after incubation has been allowed to occur. It will be seen from the figure, that most of the antigens 21 and 21a, respectively, have competitively bound to the antibodies 14.

Referring to FIG. 1d, the excess or unbound antigens 21 and 21a, respectively, are washed from between electrodes 10 and 11 as shown by arrows 24, by an aqueous electrolyte wash solution, part of which is retained between the electrodes 10 and 11 after the wash.

FIG. 1e illustrates the apparatus of FIG. 1 with the incubated and washed mixture 23 disposed in the electrolytic solution, all disposed between electrodes 10 and 11. A chemiluminescent immunoassay measurement is now ready to be made.

The switch 13 is closed for a given period of time to apply a potential across electrodes 10 and 11. The electrical potential is sufficient to generate oxidizing species such as hydrogen peroxide ($H_2O_2$) and/or monotomic oxygen (O) at the surface 16 of the electrode 10. The generation of the oxygen at surface 16 will bathe the labelled antigens 21a by spreading through the interstices 25 in the antibodies 14 attached to electrode surface 16, thus causing chemiluminescence.

The generation of an oxidant in the electrolyte may be accomplished by electrolysis at the anode electrode 10, according to the following reaction:

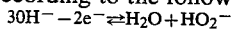
$$3OH^- - 2e^- \rightleftharpoons H_2O + HO_2^-$$

This is a situation in which gaseous $O_2$ is not necessarily liberated but peroxide and/or monatomic oxygen are produced at the electrode surface. Although it is uncertain as to which species is responsible, an oxidizing species is liberated upon application of electricity which oxidizes the chemiluminescent label and allows it to produce light.

The chemiluminescence of the labelled antigens 21a is measured by the photoelectron multiplier tube 15, which receives the emitted photons as shown by arrows 27.

The generation and the delivery of the oxidant is precisely and accurately controlled in that the potential applied to the electrodes 10 and 11 is accurately maintained over a given time interval, and the oxidant generated is directly applied to the bound chemiluminescently-labelled antigens 21a.

The chemiluminescence which results from the precise triggering (oxidation) of the chemiluminescent label bound to antigens 21a is precisely measured, because the entire reaction occurs between electrode surfaces 16 and 17. The electrodes 10 and 11 are preferably circular in shape to conform to the shape of photoelectron multiplier tube 15; the respective diameters of electrodes 10 and 11 being much greater than the distance separating them. As such, minimal light energy is lost at the periphery of electrodes 10 and 11, and photons are detected over a large solid angle.

Figure 2A:
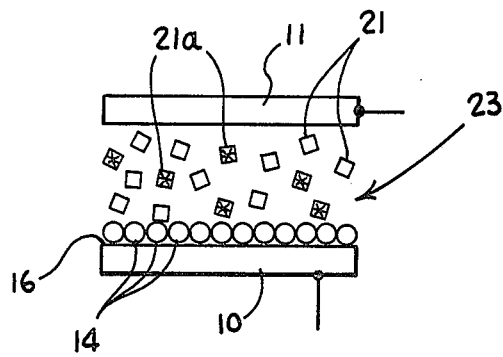
FIGS. 2a through 2g are schematic diagrams depicting how the apparatus of FIG. 1 can be used to perform a chemiluminescent assay which does not require a wash or separation step.
Figures 2B, 2C:
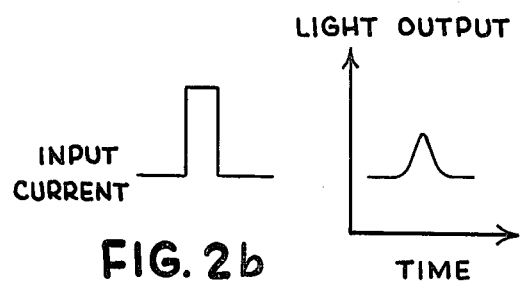

FIGS. 2a through 2g illustrate apparatus for performing an immunoassay which does not require a wash or separating step. FIG. 2a depicts the apparatus similar to that of FIG. 1 (partial view) initially receiving the immunoreactant solution 23 prior to incubation, similar to that shown for FIG. 1b. When switch 13 is closed for a short interval of time, electrodes 10 and 11 receive a short pulse of current, as shown in FIG. 2b. Immunological binding has yet to take place and, therefore, there should not be any light output from any labelled antigens 21a bound to antibodies 14. However, some labelled antigens 21a may have come close enough to the surface 16 of the anode 11 to provide a light output by the generated oxidant at surface 16. Such a light output is converted to an electrical signal by photomultiplier tube 15 (FIG. 1), as shown in FIG. 2c, and stored, and is indicative of the background level of light due to free labelled antigens 21a in solution 23.

Figure 2D:
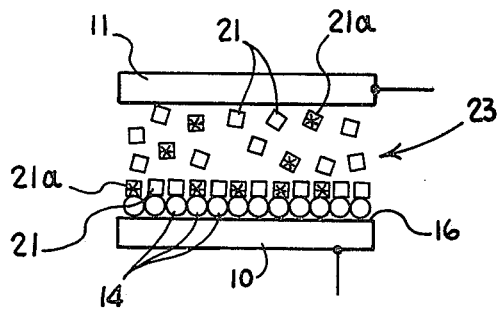
Figures 2E, 2F:
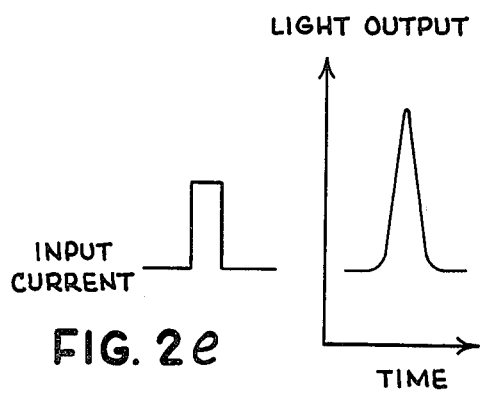

FIG. 2d illustrates the apparatus of FIG. 2a after incubation has been allowed to occur and the competitive binding reaction has been completed. Accordingly, antigens 21 and 21a are bound to antibodies 14, as shown and some free antigens 21 and 21a are in solution 23. A short input current pulse is now impressed upon electrodes 10 and 11, as shown in FIG. 2e, by the closing of switch 13 (FIG. 1) after a given time interval necessary to generate the oxidant. The labelled antigens 21a bound to antibodies 14 will emit a light output due to the oxidant generated at surface 16 of anode 10, along with any free labelled antigens 21a in solution 23 in close proximity to surface 16. This combined light output is schematically illustrated in FIG. 2f.

Figure 2G:
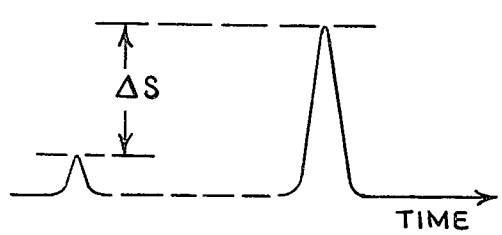

The light outputs of FIGS. 2c and 2f, respectively, are converted to electrical signals by photoelectron multiplier tube 15 (FIG. 1) and stored. The difference "ΔS" between the outputs, as depicted in FIG. 2g, is obtained by conventional comparison techniques. The difference "ΔS" is the measure of the reaction minus any background effects, and is obtained without a separation step.

FIGS. 3a through 3f illustrate still another embodiment of the invention which eliminates the need for a wash or separation step. The surface 17 of electrode 11 comprises immobilized antibodies 14a, which are not specific to the antigens 21 and 21a in solution 23. However, the antibodies 14a are selected to present a similar surface profile to the antigens 21 and 21a in solution 23 as do the antibodies 14 on surface 16 of electrode 10. Also, switch 13 of FIG. 1 (not shown) is also modified to reverse the direction of current flow between electrodes 10 and 11 (double pole switch).

The apparatus of FIG. 3a assumes that it is not always possible to introduce solution 23 between the electrodes 10 and 11, respectively, and obtain an initial light output signal due entirely to free labelled antigens 21a, i.e., some binding may have taken place upon solution introduction. Therefore, FIGS. 3a through 3f achieve a separation-free immunoassay which obtains a background signal notwithstanding some initial binding between antigens 21a and antibodies 14.

In FIGS. 3a through 3f, solution 23 is introduced between the modified electrode 11 and electrode 10, as shown in FIG. 3a. Modified switch 13 (not shown) is thrown to a first position of duration $\Delta t_1$ as indicated by pulse 30 (FIG. 3b), as as to positively charge electrode 11, thus generating oxidant at surface 17. A light output 31 (FIG. 3c) obtained from the first pulse 30 (FIG. 3b; interval $\Delta t_1$) is due only to any background antigen 21a, i.e., no light output is generated by bound antigens 21a and antibodies 14a. This is so, because the antibodies 14a do not bind to antigens 21a (i.e., are not specific for the antigen). Therefore, light output 31 is entirely due to any free labelled antigen 21a which migrated close enough to surface 17 of electrode 11 to become oxidized by the generated oxidant.

Subsequently, switch 13 is reversed to a second position (not shown) to provide a positive pulse 32 of duration $\Delta t_2$ to electrode 10. The duration $\Delta t_2$ of the pulse 32 is equal to the duration $\Delta t_1$ of pulse 30, whereby equal amounts of oxidant have been generated at surface 17 of electrode 10. The output signal 33 (FIG. 3c) is slightly greater than output signal 31, due to some initial binding of the antigens 21a with antibodies 14. Output signal 31 is subtracted from output 33, by conventional techniques, to obtain a measure for any initial binding minus the background "noise."

The last three stages of the present method are depicted by FIGS. 3d through 3f. In FIG. 3d, the solution 23 has been incubated, whereby antigens 21 and 21a have competitively bound with antibodies 14 on surface 16 of electrode 10. Switch 13 is closed to provide a positive pulse 34 to electrode 10, as shown in FIG. 3e. The resultant light output signal 35, depicted in FIG. 3f, will be a measure of the competitive binding reaction that has taken place during incubation (FIG. 3d) and any background due to free labelled antigen 21a in solution 23.

In order to obtain the true measurement of the amount of antigen, signal 31 is subtracted from signal 35, by conventional techniques. Also, a kinetic measurement is obtained by subtracting signal 31 from signal 33 for the first reading (at an early time) and, also, subtracting signal 33 from signal 35 (for a reading at a later time).

An example of two antibodies which have similar molecular profiles but are not specific to the same antigens are albumin and digoxin antibodies. Antibodies having similar molecular structure (or profiles) are chosen in the above method, so that the subtracted background signal 31 generated at electrode surface 17, will be in all respects similar to the signal 33 generated at electrode surface 16, less any possible binding output generated by the initial reaction between antigens 21a and antibodies 14.

Figure 4A:
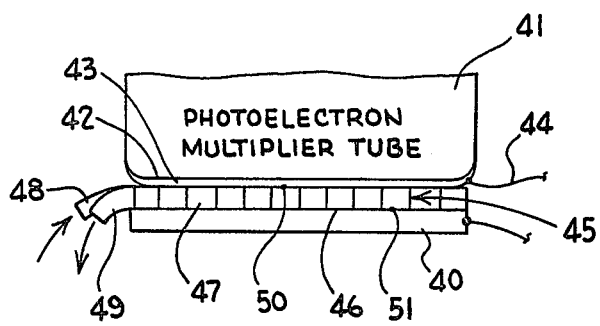
FIGS. 4a and 4b illustrate a side and plan view of a continuous flow embodiment for the apparatus of FIG. 1.
Figure 4B:
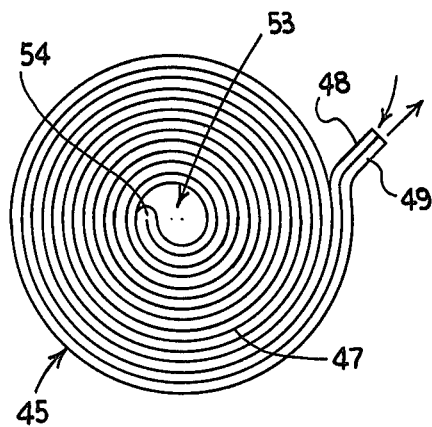

Referring to FIGS. 4a and 4b, a partial side and partial plan views, respectively, are shown of a continuous-flow embodiment of the invention. The continuous-flow embodiment comprises an anode 40 and a cathode combined with a photoelectron multiplier tube, designated as 41. The surface 42 of the photoelectron multiplier tube 41 is coated with a thin light transmissive conductive metal 43, which is coupled via contact 44 to one of the terminals of the voltage source 12 (FIG. 1), to provide an electrode/detector combination, as previously described.

A flow tube helix 45 is sandwiched between electrodes 40 and 41, shown in plan view in FIG. 4b. Helix 45 comprises a tube 47, which spirals towards the center 53 and doubles back upon itself at point 54, such that the input part 48 lies adjacent the output part 49. The upper wall 50 of tube 47 is defined by the metal surface 43 of the photoelectron multiplier tube 41, such that the helix 45 is an integral part of the photoelectron multiplier tube 41. The lower wall 51 of the helix 45 is defined by surface 46 of electrode 40, such that the helix is also an integral part of electrode 40.

A mixture of antigens 21 and 21a and antibodies 14 (the antibodies now being free in solution) is flowed along tube 47, by pumping means (not shown). The mixture is initially introduced at input port 48 and is allowed to fill the entire tube 47 until the mixture presents itself at the output port 49. Then, the flow is terminated. A voltage is applied across electrodes 40 and 41, and the level of chemiluminescence is measured by the phtoelectron multiplier tube (not shown). The reactive mixture which has been measured is then discharged through output port 49 to waste, and a new reactive mixture is introduced into input port 48 for test. The successive reactive mixtures can be mixed and incubated prior to their individual introduction into input port 48.

Consistent with the above teachings, a kinetic measurement may also be conducted with the apparatuses shown in FIGS. 3a–3g and 4a–4f. Two competing immunoreactants are mixed (one of the immunoreactants having a chemiluminescent label) and introduced between the electrodes 10 and 11. The electrodes 10 and 11 are periodically pulsed, as described, during incubation to produce oxidant. In this manner, the reaction is continuously monitored to obtain chemiluminescent light levels that are indicative of the kinetic rate of reaction of the immunoassay, as described.

Now referring to FIG. 5, still another embodiment of the invention is shown, wherein tube 47 disposed between electrodes 40 and 41, respectively, is compartmentalized to define a number of reactive chambers, e.g., 1a–10a. Each chamber includes corresponding input ports 1b–10b and output ports 1c–10c, as shown. Such structure is operated similarly to that of FIGS. 4a and 4b. Each chamber 1a through 10a may contain a different reactive mixture, i.e., different immunoassays will be performed in each chamber, and is provided its own electrode pair. Chambers 1a–10a are electrically isolated so that each chamber may be individually pulsed to effect a measurement.

The chambers 1a–10a of FIG. 5 are preferably operated in sequential fashion, so that no confusion arises in the measurements. However, each chamber 1a–10a may be filled and emptied either concurrently or sequentially.

The present invention contemplates the reuse of the antibodies 14 immobilized on surface 16 of electrode 10. After the aforementioned incubation and measurement processes of FIGS. 1a–1e, 2a–2g, and 3a–3f, antigens 21 and 21a bound to the antibodies 14 of electrode 10 can be lysed or otherwise released from the antibodies 14, so that antibodies 14 are available for a subsequent immunoassay.

The lysing or releasing of the bound antigens can be accomplished in several ways:

(1) a releasing agent may be introduced to the electrode 10. The releasing agent may be a chaotropic agent, a detergent, magnesium chloride, a soluble thiocyanate salt, or a soluble citrate salt;

(2) electrical current may be applied to electrode 10 of sufficient potential to cause a release of the bound antigens; and (3) a release of the antigens may also be accomplished by changing the character of the solution such as changing its pH, its tonicity, or its temperature.

While several exemplary embodiments have been shown describing different methods of practicing the invention, the invention is not to be limited to any particular embodiment, but should be interpreted on a broader scope consistent with the appended claims.

Having described the invention, what is desired to be protected by Letters Patent is presented by the following claims.

What is claimed is:

1. A method of immunoassaying a sample containing an immunoreactant comprising the steps of:
    (a) forming a reaction mixture comprising said sample immunoreactant, a complementary immunoreactant, and a competitive immunoreactant with respect to said sample immunoreactant, said competitive immunoreactant having a chemiluminescent label attached thereto;
    (b) confining said reaction mixture between a pair of electrodes;
    (c) immobilizing said complementary immunoreactant adjacent one of said electrodes prior to the confining of said reaction mixture;
    (d) incubating said reaction mixture to form a reaction product;
    (e) applying a controlled voltage across said pair of electrodes for a controlled period of time to generate an oxidant for chemically triggering said chemiluminescently labelled competitive immunoreactant bound to said complementary immunoreactant in said reaction product; and
    (f) measuring the chemiluminescence of said bound chemiluminescently labelled competitive immunoreactant.

2. The method of claim 1, wherein said applying step comprises applying said controlled voltage across said pair of electrodes prior to and/or during said incubation step and said measuring step comprises measuring said chemiluminescence during application of said controlled voltage.

3. The method of claim 1, wherein the step of immobilizing comprises immobilizing said complementary immunoreactant on the surface of said one of said electrodes.

4. The method of claim 1, wherein the step of immobilizing comprises immobilizing said complementary immunoreactant on a membrane adjacent said one electrode.

5. The method of claim 1, wherein the step of immobilizing comprises containing said complementary immunoreactant within a gel layer disposed adjacent the surface of said one electrode.

6. The method of claim 1, further comprising the step of:
    (g) washing away any excess immunoreactants from between said pair of electrodes after said incubating step and prior to said measuring step.

7. The method of claim 1, further comprising the step of:
    (g) releasing said bound chemiluminescently labelled competitive immunoreactant from said immobilized complementary immunoreactant following said measuring step.

8. The method of claim 7, wherein said releasing step comprises changing the pH of the said reaction mixture.

9. The method of claim 7, wherein said releasing step comprises changing the tonicity of said reaction mixture.

10. The method of claim 7, wherein said releasing step comprises changing the temperature of said reaction mixture.

11. The method of claim 7, wherein said releasing step comprises applying a second voltage across said pair of electrodes.

12. The method of claim 7, wherein said releasing step comprises introducing a releasing agent into said mixture.

13. The method of claim 7, wherein said releasing agent is chaotronic.

14. The method of claim 13, wherein said releasing agent comprises a detergent.

15. The method of claim 13, wherein said releasing agent is selected from a group consisting of: magnesium chloride, a soluble thiocyanate salt and a soluble citrate salt.

16. Apparatus for conducting an immunoassay, comprising:
    first and second metallic electrodes defining first and second opposing surfaces, respectively, said first electrode defining an anode and supporting a first immunoreactant on said first surface, and at least one of said electrodes being light transmissive;
    means for introducing a reactive solution between said first and second surfaces comprising at least second and third immunoreactants, said second immunoreactant being competitive with said first immunoreactant with respect to binding with said third immunoreactant, said second immunoreactant being labelled with chemiluminescent substance;
    means for impressing an electrical potential across said first and second electrodes for generating an oxidant at said first surface to oxidize said chemiluminescent substance; and
    means for measuring the chemiluminescence of said chemiluminescent substance, said measuring means comprising a detector means disposed adjacent said one electrode for receiving chemiluminescent radiation generated by oxidation of said chemiluminescent substance.

17. The apparatus of claim 16, wherein said first electrode comprises a membrane to which said first immunoreactant is bound.

18. The apparatus of claim 16, wherein said first electrode comprises a gel layer containing said first immunoreactant.

19. The apparatus of claim 18, wherein said one electrode is integrally formed with said detector means.

20. The apparatus of claim 16, wherein said introducing means comprises a tubular structure having a spiral configuration disposed between said first and second electrodes.

21. The apparatus of claim 20, wherein said tubular structure defines a plurality of reaction compartments disposed between said first and second electrodes.

* * * * *